US010793892B2

(12) United States Patent
Nordmann et al.

(10) Patent No.: US 10,793,892 B2
(45) Date of Patent: *Oct. 6, 2020

(54) METHOD FOR DETECTING THE PRESENCE OF EXPANDED SPECTRUM β-LACTAMASE-PRODUCING BACTERIA IN A SAMPLE

(71) Applicants: INSERM (INSTITUT NATIONAL DE LA SANTE ET DE LA RECHERCHE MEDICALE), Paris (FR); UNIVERSITE PARIS-SUD XI, Orsay (FR); ASSISTANTE PUBLIQUE HOPITAUX DE PARIS (APHP), Paris (FR)

(72) Inventors: Patrice Nordmann, Le Kremlin Bicetre (FR); Laurent Dortet, Le Kremlin Bicetre (FR); Laurent Poirel, Le Kremlin Bicetre (FR)

(73) Assignees: INSERM (INSTITUT NATIONAL DE LA SANTE ET DE LA RECHERCHE MEDICALE), Paris (FR); UNIVERSITÉ PARIS-SACLAY, Saint-Aubin (FR); ASSISTANTE PUBLIQUE HOPITAUX DE PARIS (APHP), Paris (FR)

( * ) Notice: Subject to any disclaimer, the term of this patent is extended or adjusted under 35 U.S.C. 154(b) by 545 days.

This patent is subject to a terminal disclaimer.

(21) Appl. No.: 14/358,839

(22) PCT Filed: Nov. 16, 2012

(86) PCT No.: PCT/EP2012/072908
§ 371 (c)(1),
(2) Date: May 16, 2014

(87) PCT Pub. No.: WO2013/072494
PCT Pub. Date: May 23, 2013

(65) Prior Publication Data
US 2014/0308693 A1 Oct. 16, 2014

(30) Foreign Application Priority Data
Nov. 18, 2011 (EP) ...................................... 11306516

(51) Int. Cl.
C12Q 1/34 (2006.01)
C12Q 1/00 (2006.01)
C12Q 1/04 (2006.01)

(52) U.S. Cl.
CPC .................. *C12Q 1/34* (2013.01); *C12Q 1/00* (2013.01); *C12Q 1/04* (2013.01)

(58) Field of Classification Search
None
See application file for complete search history.

(56) References Cited

U.S. PATENT DOCUMENTS

2009/0117601 A1* 5/2009 Yang-Woytowitz et al. ................
C12Q 1/04
435/18

FOREIGN PATENT DOCUMENTS

| GB | 2 462 186 A | 2/2010 | |
| GB | 2462186 A * | 2/2010 | ....... G01N 33/56938 |
| WO | 2004/063391 A1 | 7/2004 | |
| WO | 2010/010083 A1 | 1/2010 | |
| WO | WO-2010010083 A1 * | 1/2010 | ............. C12Q 1/045 |

OTHER PUBLICATIONS

Escamilla, J., Antimicrobial Agents and Chemotherapy, pp. 196-198; 1976 (of record).*
Escamilla, "Susceptibility of Haemophilus influenza to ampicillin as determined by use of a modified one-minute beta-lactamase test", Antimicrobial Agents and Chemotherapy, Jan. 1, 1976, pp. 196-198, vol. 9, No. 1, American Society for Microbiology, Washington, DC, US.
Olsson et al., "Formation of beta-lactamase in Bacteroides fragilis: cell-bound and extracellular activity", Antimicrobial Agents and Chemotherapy, May 1, 1976, pp. 727-735, vol. 9, No. 5.

(Continued)

*Primary Examiner* — Sharmila G Landau
*Assistant Examiner* — Paul D. Pyla
(74) *Attorney, Agent, or Firm* — W&C IP (57) ABSTRACT

The present invention relates to a method for detecting the presence of expanded-spectrum ß-lactamase (ß-lactamase hydrolyzing expanded-spectrum cephalosporin)-producing bacteria in a sample, said method comprising the steps of: a) performing cell lysis on a test sample in order to obtain an enzymatic suspension; b) reacting a fraction of the enzymatic suspension obtained in step a) with a reagent kit, said reagent kit comprising —expanded-spectrum ß-lactamase substrate selected from the group consisting of cephalosporins, aztreonam, and cephamycins, —a pH color indicator which will change color when the pH of the reaction mixture is comprised between 6.4 and 8.4, wherein a color change after step b) indicates the presence of expanded-spectrum ß-lactamase-producing bacteria in the test sample. The invention also relates to a reagent kit, to a microtiter plate and to their uses in detecting the presence of expanded-spectrum ß-lactamase producers in a test sample.

8 Claims, 2 Drawing Sheets

(56) References Cited

OTHER PUBLICATIONS

Skinner et al., "A Comparison of 3 Rapid Methods for the Detection of Beta Haemophilus-Influenzae", Journal of Clinical Pathology (London), 1977, pp. 1030-1032, vol. 30, No. 11.

Edwards et al., "An investigation of beta-lactamases from clinical isolates of *Bacteroides* species", Journal of Medical Microbiology, Feb. 1992, pp. 89-95, vol. 36, No. 2.

Park et al., "Aciodmetric Agar Plate Method for Ampicillin Susceptibility Testing of Haemophilus-Influenzae", Antimicrobial Agents and Chemotherapy, 1978, pp. 318-320, vol. 13, No. 2.

\* cited by examiner

FIGURE 1

METHOD FOR DETECTING THE PRESENCE OF EXPANDED SPECTRUM β-LACTAMASE-PRODUCING BACTERIA IN A SAMPLE

FIELD OF THE INVENTION

The present invention relates to a method for detecting the presence of an expanded spectrum ß-lactamase (ß-lactamase that hydrolyze expanded-spectrum cephalosporins) in a clinical sample or from cultured bacteria.

BACKGROUND OF THE INVENTION

Gram-negative bacteria are important causes of hospital- and community acquired infections, *Escherichia coli* being the most important human pathogens. Multiresistant Enterobacteriaceae (*Escherichia coli, Klebsiella pneumonia, Proteus mirabilis, Serratia marscescens, Enterobacter* spp. . . . ) *Pseudomonas* sp. and *A. baumannii* are often associated with limited therapeutic options. Those multidrug resistant isolates mostly express a ß-lactamase with expanded activity towards expanded-spectrum cephalosporins such as cefotaxime, and/or ceftazidime, and/or cefepime, and/or aztreonam. Those producers of expanded-spectrum ß-lactamases may be difficult to detect using routine antibiotic susceptibility testing and may initially appear to be susceptible to several expanded-spectrum cephalosporin molecules. Inaccurate and/or delayed identification of expanded-spectrum ß-lactamases-producing bacteria has resulted in associated inappropriate selection of antimicrobial therapy and treatment failure. Therefore, a rapid and optimal detection of producers of expanded-spectrum ß-lactamase producers is of primarily importance in clinical settings The ß-lactamases are commonly classified according to two different general schemes; the Ambler molecular classification and the Bush-Jacoby-Medeiros functional classification. The Ambler scheme classifies ß-lactamases into four classes according to the protein homology of enzymes, ß-lactamases of class A, C and D are serine-ß-lactamases and class B enzymes are metallo ß-lactamases. The second classification is the Bush-Jacoby-Medeiros functional scheme based on functional properties of the enzymes. The term "extended-spectrum ß-lactamases (ESBLs) was originally applied to the TEM and SHV derivatives that can hydrolyze oxyimino cephalosporins being classified in the group 2 be with the Bush-Jacoby-Medeiros functional schemes in the 1980's. Those enzymes belong to the Ambler class A group of ß-lactamases and their activity is inhibited by class A inhibitors such as tazobactam, clavulanic acid and sulbactam. More than 700 distinct ß-lactamases have been described, many of them hydrolyzing extended-spectrum cephalosporins and belonging to each type of Ambler groups of enzymes. In addition several of those expanded-spectrum enzymes may hydrolyze not only cephalosporins but also carbapenems which are the ß-lactams with the most extended spectrum of activity.

Therefore expanded-spectrum ß-lactamases can be grouped as follows within each Ambler class of enzymes.

1—The Ambler class A enzymes; they are inhibited by clavulanic acid, tazobactam and sulbactam. These enzymes (ESBLs) are mostly of the SHV, TEM and CTX-M groups. Whereas the SHV and TEM ESBLS were mostly reported in Enterobacteriaceae (*K. pneumoniae, Enterobacter* sp.) as a source of hospital-based infections, the CTX-Ms are becoming a major threat for patients also in the community. They may be identified in up to 60 to 80% of *E. coli* isolates in certain areas of the world such as in Asia. They are identified not only in urinary tract infections which is the main source of infections due to *E. coli* but also in much more severe infections such as pneumonia and septicaemia. The CTX-Ms enzymes are mostly identified in Enterobacteriaceae on transferable plasmids. A few enzymes of that class such as the KPC enzymes may in addition hydrolyze carbapenems.

2—The Ambler class B enzymes. These enzymes possess all additional properties to hydrolyze carbapenems which is not inhibited by clavulanic acid, tazobactam and sulbactam but by addition of chelators of zinc (EDTA). These metallo ß-lactamases of mostly identified among hospital-acquired pathogens such as Enterobacteriaceae, *Pseudomonas aeruginosa* and *Acinetobacter baumannii*. They are of mostly of the IMP, VIM, and NDM types.

3—The Ambler class C enzymes or commonly known as "cephalosporinases hydrolyze expanded-spectrum cephalosporins to diverse extend. Their activity is inhibited by cloxacillin and other methicillin-related molecules as well as by boronic acid. They are identified in many enterobacterial species (*Enterobacter* sp, *Serratia, Citrobacter freundii* . . . ), *Pseudomonas aeruginosa*, and *Acinetobacter baumannii*. These chromosome-encoded enzymes are expressed at a low level to those wild-type bacterial species explaining why they remain susceptible to may expanded-spectrum cephalosporins (ceftazidime in particularly). When expressed at an high level, they confer an acquired resistance phenotype to those cephalosporins. In addition, those cephalosporinase genes may be identified on plasmids in many other enterobacterial species (*E. coli, K. pneumonia, P. mirabilis, Salmonella*) explaining a trait of acquired resistance to cephalosporins. From a clinical point of view, acquired plasmid-mediated cephalosporinases are less frequent that CTX-Ms to which they may be associated in same isolates.

4—The Ambler class D enzymes with extended ability to hydrolyze cephalosporins have been reported mostly in *Pseudomonas aeruginosa* (OXA-10 derivatives). Their activity is inhibited neither by clavulanic acid, sulbactam and tazobactam nor by EDTA.

Taking in account the importance of ESBLs in any clinical settings (acute care facilities, long term care facilities, community, detection has been focused on those ESBLs.

It is recommended that at least all clinically significant *E. coli* and *K. pneumoniae* should undergo screening for ESBLs. It is recommended that those species with MIC≥8 mg/L for cefpodoxime or MIC≥2 mg/L against ceftazidime, cefotaxime, ceftriaxone, or aztreonam should be investigated using phenotypic confirmatory tests. In those phenotypic test, susceptibility to cefotaxime, ceftazidime. alone or with class A ß-lactamase inhibitors are compared. The double disk synergy test was first proposed for that purpose. This test is performed an agar plate with a disk containing cefotaxime (30 μg) and a disk containing amoxicillin/clavulanate (20 μg/10 μg, respectively) placed 30 mm apart (center to center). Extension of inhibition zone around the cefotaxime disk towards the amoxicillin/clavulanate disk indicates production of ESBL. Disks containing other oxyimino-ß-lactams (ceftriaxone, ceftazidime, or aztreonam) can be substituted for cefotaxime diks. The "Etest®" technique is used also for detection of ESBLs. It is a quantitative technique for determining the antimicrobial susceptibility of many microorganisms. The system comprises a predefined antibiotic gradient which is used to determine the Minimum Inhibitory Concentration (MIC), in mg/L, of different antimicrobial agents against microorganisms as tested on agar media using overnight incubation. In the case of ESBL detection, the E-test strip may be impregnated with one side containing a concentration gradient of ceftazidime and the other side containing a concentration gradient of ceftazidime plus a constant concentration of clavulanate. Similar strips have been developed impregnated with cefotaxime/clavulancate or cefepime clavulanate. The results of the Etest ESBL is interpreted as positive when more than a 3-fold decrease in the MIC value of the tested drug is observed in the presence of clavulanate. Sensitivity and specificity of the double-disk test and of the E-test is quite good ranging from 80 to 95%.

Automated method for bacterial identification and susceptibility testing are used in the detection of ESBL producing organisms. The BD Phoenix system (Becton-Dickinson) uses its expert software to interpret the growth response to ceftazidime, cefotaxime, ceftriaxone and cefpodoxime with or without clavulanate. Similarly, the Vitek2 system (bioMérieux) uses a card containing ceftazidime and cefotaxime alone and in combination with clavulanate. Ceftazidime and cefotaxime plus ß-lactamase inhibitors are also used in the MicroScan Walkaway-96 system (Dade Behring). The performance of those systems varies and differs with the species investigated with a much higher sensitivity (80% to 99%) than specificity (50% to 80%).

PCR-based and other molecular techniques may also help to identify the ESBL genes but they are time consuming and expensive. Those PCR-based techniques require isolation of bacteria from clinical samples prior to susceptibility testing and phenotypic identification. Therefore, those results can be obtained at the best 48 hours after obtention the clinical samples. They are usually not performed in a routine lab but restricted to epidemiological purposes.

Since patients with infections due to ESBL-producing enterobacteria tended to have less satisfactory outcomes than those infected with pathogens that do not produce ESBLs, it is important to detect as early as possible those ESBL producers.

To facilitative the detection of expanded-spectrum ß-lactamase (ESBL in particularly) producers in the field of clinical microbiology, the Applicant has developed a new method based on a simple acido-colorimetric technique. This method is based on the concept that by hydrolysing the beta-lactam ring of an expanded-cephalosporin substrate, the enzymes generate a carboxyl group which in turn acidifies a medium. The acidity resulting from this hydrolysis is then identified by a color change of a pH color indicator.

This method helps differentiate the expanded-spectrum ß-lactamase producers from those that are not producers.

Interpretable results are obtained within a very short time, which is crucial when designing treatment of producers. It eliminates the need of using the phenotypic techniques mentioned above.

This method offers a solution for fast, reliable and affordable detection of expanded-spectrum ß-lactamase-producers in particularly of ESBL producers. It may also be submitted to an industrialization process such that it may be implemented in any clinical microbiology laboratory worldwide without significant additional workload for laboratory technicians. It can be used directly with clinical samples and not only on bacterial grown at the stage of colony.

Moreover, in the field of epidemiology, the use of this method may be of further help when wanting to rapidly select strains which should be tested by PCR and sequenced for identification of expanded-spectrum ß-lactamase genes.

SUMMARY OF THE INVENTION

The present invention relates to a method for detecting the presence of expanded-ß-lactamase producing in a sample, said method comprising the steps of:
a) performing cell lysis on a test sample in order to obtain an enzymatic suspension;
b) reacting a fraction of the enzymatic suspension obtained in step a) with a reagent kit, said reagent kit comprising
   An expanded-spectrum cephalosporin or aztreonm as a substrate
   a pH color indicator which will change color when the pH of the reaction mixture is comprised between 6.4 and 8.4
wherein a color change after step b) indicates the presence of ESBL- or a non ESBL expanded-spectrum ß-lactamase-producing bacteria in the test sample.

The present invention also relates to a reagent kit comprising an expanded-spectrum cephalosporin or aztreonm or cephalosporinase substrate selected from the group consisting of cephalosporins and cephamycins and a pH color indicator and its use in detecting the presence of ESBL and or a non-ESBL expanded-spectrum ß-lactamase-producing bacteria in a test sample.

The invention also relates to a microtiter plate comprising a well or a series of wells comprising a carbapenemase substrate selected from the group consisting of cephalosporins or aztreonam, its use in detecting the presence of ESBL and/or non-ESBL expanded-spectrum ß-lactamase-producing bacteria in a test sample and it use in eventually determining the specific class of expanded-spectrum ß-lactamase-producing bacteria present in a test sample.

DETAILED DESCRIPTION OF THE INVENTION

Definitions

As used herein, "test sample" means any liquid or solid material to be tested which may contain ESBL- or non ESBL expanded-spectrum ß-lactamase-producing bacteria. Typically, a bacterial colony may be isolated from such a material. The preferred "test sample" is a biological sample.

As used herein, "biological sample" means any biological sample obtained from a subject. Examples of such "biological samples" include fluids, tissues, cell samples, etc. Preferred "biological samples" are whole blood, serum, plasma or urine.

As used herein, "subject" denotes a mammal, such as a rodent, a feline, a canine, and a primate. Preferably a "subject" according to the invention is a human.

As used herein, "pH color indicator" is a halochromic chemical compound that is added in small amounts to a solution so that the pH of the solution/medium can be determined visually. The indicator causes the color of the solution/medium to change depending on the pH.

As used herein, "enzymatic suspension" means that the step of cell lysis (step a) of the method according to the invention) helps liberate enzymes which are present within the cells of the test sample, thereby obtaining an "enzymatic suspension".

As used herein, "fraction" means that all or part of the enzymatic suspension obtained in step a) of the method according to the invention is taken in order to be reacted with the reagent kit in step b). Typically, a "fraction" according to the invention is a part of the enzymatic suspension. Preferably, a "fraction" according to the invention is 10 µL to 50 µL.

As used herein, a "kit" means a product comprising a number of different components, as a combination product, for separate, simultaneous or sequential use in the method of the invention. Preferably, the components are a ESBL- or non ESBL expanded-spectrum ß-lactamase-producing bacteria substrate selected from the group consisting of cephalosporins and aztreonam, a pH color indicator, optionally an ESBL inhibitor.

Detection Method:

As previously mentioned, early detection of ESBL and non-ESBL expanded-spectrum ß-lactamase-producing bacteria is becoming a major issue in the field of clinical microbiology in order to prevent their spread and rapidly adapt the antibiotic therapy to treat severe infections.

As a solution to this problem, the Applicant has developed a fast, reliable and affordable method for detecting any type of expanded-spectrum ß-lactamase-producing bacteria producers.

The present invention therefore relates to a method for detecting the presence of ESBL and or non-ESBL expanded-spectrum ß-lactamase-producing bacteria in a sample, said method comprising the steps of:
a) performing cell lysis on a test sample in order to obtain an enzymatic suspension;
b) reacting a fraction of the enzymatic suspension obtained in step a) with a reagent kit, said reagent kit comprising
   an expanded-spectrum ß-lactamase-producing bacteria selected from the group consisting of cephalosporins and aztreonam,
   a pH color indicator which will change color when the pH of the reaction mixture is comprised between 6.4 and 8.4,
wherein a color change after step b) indicates the presence of expanded-spectrum ß-lactamase-producing bacteria in the test sample.

The method of the invention is based on the concept that by hydrolysing the beta-lactam by an expanded-spectrum ß-lactamase-producing bacteria substrate, which generates a carboxyl group which in turn acidifies a medium, typically an unbuffered medium. The acidity resulting from this hydrolysis is then identified by a color change of a pH color indicator. A change in color indicates the presence of a expanded-spectrum ß-lactamase-producing bacteria.

Typically, a broth is inoculated with a test strain (obtained from a test sample) and incubated on a rotative shaker. Then, the culture is centrifuged and the pellet resuspended in a lysis buffer, vortexed and further incubated (similarly, a direct lysis protocol, known to the skilled person in the art, can be applied using bacterial colonies grown on solid culture medium). After sufficient incubation, the suspension (i.e. enzymatic suspension) is centrifuged and the supernatant is removed and placed on ice. A small fraction of this supernatant is mixed with a reagent kit comprising a expanded-spectrum ß-lactamase-producing bacteria substrate and a pH color indicator. The mixture composed of the reagent kit and the tested enzymatic suspension is further incubated at a temperature and for a sufficient amount of time such that a change of color is observed. A change of color indicates the presence of an expanded-spectrum ß-lactamase-producing bacteria. The color change may be obtained as early as 5 minutes after starting the incubation.

In most cases, a 30 minutes incubation time is sufficient for obtaining a frank color change for expanded-spectrum ß-lactamase producers.

Typically, the use of this method may be of further help when wanting to rapidly select strains which should be tested by PCR and sequenced for identification of expanded-spectrum ß-lactamase-producing bacteria. Consequently, once the presence of expanded-spectrum ß-lactamase-producing bacteria has been determined by the present method, other identification techniques known to the skilled person in the art may be used to further characterize enzymes.

Typically, once an expanded-spectrum ß-lactamase-producing bacteria has been detected by the method of the invention, this expanded-spectrum ß-lactamase-producing bacteria activity may be further used to discover or evaluate novel inhibitors or novel molecules resistant to the activity of expanded-spectrum ß-lactamase-producing bacteria. In the latter case, the novel molecule to be evaluated may replace the expanded-spectrum ß-lactamase substrate molecule contained in the reagent kit.

Typically, the method according to the present invention may be used to detect any or expanded-spectrum ß-lactamase-producing bacteria selected from the group consisting of gram positive and gram negative bacteria. Preferably, the expanded-spectrum ß-lactamase-producing bacteria are selected from the group consisting of bacteria which are of clinical importance and even more preferably from the group consisting of gram negative bacteria which are of clinical importance.

As used herein, bacteria of "clinical importance" means bacteria involved in nosocomial and community-acquired infections.

Typically, the expanded-spectrum ß-lactamase-producing bacteria are selected from the genera consisting of *Acinetobacter, Aeromonas, Bacillus, Bacteroides, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella* and *Strenotrophomonas*.

Typically, the expanded-spectrum ß-lactamase-producing bacteria are selected from the group consisting of *Acinetobacter baumannii, Aeromonas junii, Bacillus cereus, Bacteroides fragilis, Citrobacter amalonaticus, Citrobacter freundii, Citrobacter youngae, Enterobacter aerogenes, Enterobacter asburiae, Enterobacter cloacae, Escherichia coli, Klebsiella oxytoca, Klebsiella pneumoniae, Morganella morganii, Pandoraea pnomenusa, Proteus mirabilis, Proteus rettgeri, Proteus vulgaris, Providencia stuartii, Pseudomonas aeruginosa, Salmonella enterica, Serratia marcescens, Shigella flexneri, Strenotrophomonas maltophilia, Ralstonia picketti* and *Shewanella algae*.

According to the present invention, the expanded-spectrum ß-lactamase-producing bacteria are preferably selected from the genera consisting of *Acinetobacter, Enterobacter, Escherichia, Klebsiella, Pseudomonas*, and even more preferably selected from the group consisting of *Acinetobacter baumannii, Escherichia coli, Klebsiella pneumoniae* and *Pseudomonas aeruginosa*.

As used herein according to the present invention, an expanded-spectrum ß-lactamase substrate is one which is selected from the group consisting of cephalosporins, aztreonam, and cephamycins.

Typically, the cephalosporins is selected from the group consisting of cefotaxime, ceftazidime, ceftriaxone, cefepime, cefpirome and aztreonam.

Typically, the cephamycin is selected from the group consisting of moxalactam and cefoxitin. Cephamycins are particularly interesting for the detection of several types of non-ESBLs expanded-spectrum ß-lactamases.

Preferably, the expanded-spectrum ß-lactamase substrate is cefotaxime.

Typically, the concentration of ß-lactamase substrate used in the reagent kit is comprised between 0.1 mg/ml and 10 mg/ml, more preferably between 1 mg/ml and 5 mg/ml and even more preferably between 3 mg/ml and 4 mg/ml.

According to the invention, the pH color indicator will change color when the pH of the reaction mixture is comprised between 6.4 and 8.4, preferably between 6.6 and 7.5.

Typically, the concentration of pH color indicator used in the reagent kit is comprised between 0.01% and 1%, more preferably between 0.03% and 0.08% and even more preferably between 0.05% and 0.06%.

Typically, the skilled person in the art is able to select a proper pH color indicator for this hydrolysis reaction. A list of pH indicators which may be used in the present invention can be found in the CRC Handbook of Chemistry and Physics: A Ready-reference Book of Chemical and Physical Data, $91^{st}$ Revised ed. (Jun. 1, 2010), CRC Press Inc. For example, the pH color indicator used in the present invention may be selected from the group consisting of 6,8-dinitro-2,4-(1H)quinazolinedione (pH: 6.4 to 8.0), bright yellow (pH: 6.6 to 7.8), phenol red (pH: 6.6 to 8.0) and neutral red (pH: 6.8 to 8.0).

Preferably, the pH color indicator used in the present invention is phenol red and when it is used a color change from red to yellow indicates the presence of ESBL or non-ESBL expanded-spectrum ß-lactamase-producing bacteria in the test sample.

Typically, the reaction in step b) is carried out over a period of time sufficient to observe a color change. Preferably, the color change is visually observed within a time period comprised between 5 minutes and 120 minutes, preferably between 10 and 60 minutes, more preferably between 20 and 40 minutes. Alternatively, identification of the color change may be automatised by using a photometer for example.

Typically, the reaction in step b) is carried out at a temperature comprised between 15° C. and 40° C., preferably between 18° C. and 37° C., more preferably between 20° C. and 37° C.

Based on molecular studies, ESBL and non-ESBL expanded-spectrum ß-lactamases can be further divided into four types according to the Ambler classification:
  Ambler class A enzymes ("ESBLs")
  Ambler class B enzymes (metallo-ß-lactamases)
  Ambler class C enzymes ("cephalosporinases")
  Ambler class D enzymes ("oxacillinases")

Typically, a broth is inoculated with a test strain (obtained from a test sample) and incubated on a rotative shaker. Then, the culture is centrifuged and the pellet resuspended in a lysis buffer, vortexed and further incubated. After sufficient incubation, the suspension (i.e. enzymatic suspension) is centrifuged and the supernatant is removed and placed on ice. A small fraction of this supernatant is mixed with a reagent kit comprising an expanded-spectrum ß-lactamase substrate, a pH color indicator. The mixture composed of the reagent kit and the tested enzymatic suspension is further incubated at a temperature and for a sufficient amount of time such that a change of color is observed. A change of color indicates the presence of expanded-spectrum ß-lactamase-producing bacteria. The color change may be obtained as early as 5 minutes after starting the incubation. In most cases, a 30 minutes incubation time is sufficient for obtaining a frank color change for at least ESBL producers.

In a preferred embodiment, there is provided a method for detecting the presence of expanded-spectrum ß-lactamase-producing bacteria in a biological sample, said method comprising the steps of:
a) performing cell lysis on a biological sample in order to obtain an enzymatic suspension;
b) reacting a fraction of the enzymatic suspension obtained in step a) with a reagent kit, said reagent kit comprising
  cefotaxime as the expanded-spectrum ß-lactamase substrate, and
  phenol red as the pH color indicator,
wherein a color change from red to yellow after step b) indicates the presence of an expanded-spectrum ß-lactamase-producing the biological sample.

According to an embodiment, in order to specifically identify the class of or the expanded-spectrum ß-lactamase-producing bacteria which is present in the test sample, whether an Ambler Class A, B, C, D ß-lactamase, a ß-lactamase inhibitor may be used.

Typically, the ß-lactamase inhibitor may be mono-specific for one class of ß-lactamase. For example, ß-lactamase inhibitors are selected from the group consisting of clavulanic acid, tazobactam, sulbactam, and aminophenylboronic acid for ß-lactamase of Ambler class A, and selected from the group consisting of group M penicillins for ß-lactamase of Ambler class C.

In a preferred embodiment, the mono-specific inhibitor for ß-lactamase of Ambler class A is tazobactam.

In a preferred embodiment, the mono-specific ß-lactamase inhibitor for ß-lactamases of Ambler class B is EDTA more or less associated with zinc depletion.

In a preferred embodiment, the mono-specific ß-lactamase inhibitor for ß-lactamases of Ambler class C is cloxacillin or oxacillin.

Typically, the carbapenemase inhibitor may be bi-specific for more than one class of enzymes, such as for example NXL-104 which is bi-specific for carbapenemases of Ambler classes A and D.

Typically, the concentration of mono-specific ß-lactamase inhibitor for ß-lactamase of Ambler class A (such as for example tazobactam) is comprised between 0.1 mg/ml and 10 mg/ml, more preferably between 1 mg/ml and 5 mg/ml and even more preferably between 2 mg/ml and 4 mg/ml.

Typically, the concentration of mono-specific carbapenemase inhibitor for carbapenemases of Ambler class B (such as for example EDTA) is comprised between 0.001 M and 0.5 M, more preferably between 0.001 M and 0.01 M and even more preferably at 0.005 M.

Typically, the concentration of mono-specific ß-lactamase inhibitor for ß-lactamases of Ambler class C (such as for example cloxacillin and oxacillin) is comprised between 0.1 mg/ml and 10 mg/ml, more preferably between 1 mg/ml and 5 mg/ml and even more preferably between 2 mg/ml and 4 mg/ml.

Typically, the concentration of bi-specific ß-lactamase inhibitor for ß-lactamases of Ambler classes A and D (such as for example NXL-104) is comprised between 0.05 mg/ml and 10 mg/ml, more preferably between 1 mg/ml and 8 mg/ml and even more preferably between 3 mg/L and 5 mg/ml.

Typically, in order to identify the class of expanded-spectrum ß-lactamase, one may use a 96-well microtiter plate and divide the plate in four sections. In a first section, the presence of expanded-spectrum ß-lactamase-producing bacteria may be detected according to the method of the invention as described previously. In a second section, ESBL of Ambler class A may be detected by adding a ß-lactamase inhibitor for ß-lactamase of classes A. In a third section, metallo-ß-lactamases of Ambler class B may be detected by adding a ß-lactamase inhibitor for ß-lactamase of classes B. In a fourth section, cephalosporinases of Ambler class C may be detected by adding a ß-lactamase inhibitor for ß-lactamase of classes C. Finally, in a fifth section, ß-lactamase of Ambler class D may be detected by adding a ß-lactamase inhibitor for carbapenemases of class D. Depending on the ß-lactamase inhibitor used, the skilled person in the art is then able, by simple deduction, to establish the specific Ambler class(es) of expanded-spectrum ß-lactamase which is(are) present in the test sample.

Typically, the ß-lactamase inhibitor may be part of the reagent kit itself and thus added at the same time as the expanded-spectrum ß-lactamase substrate, the pH color indicator.

Alternatively, the ß-lactamase inhibitor may be separate from the reagent kit and thus added simultaneously or sequentially to the reagent kit and/or the test sample (fraction of the enzymatic suspension).

Once, the method according to the invention has been performed in all of the four sections, that is, with or without the ß-lactamase inhibitors, a comparison is established between results obtained after performing the method as described above and results obtained after performing the same method in which a ß-lactamase inhibitor was further added.

Reagent Kit:

According to another aspect of the invention, there is provided a reagent kit comprising an expanded-spectrum ß-lactamase-producing bacteria substrate selected from the group consisting of cephalosporins, aztreonam and cephamycins and a pH color indicator.

According to an embodiment of the invention, the reagent kit may comprise an expanded-spectrum ß-lactamase substrate, a pH color indicator.

According to an embodiment of the invention, the reagent kit may further comprise a ß-lactamase inhibitor. Thus, the reagent kit may comprise an expanded-spectrum ß-lactamase substrate a pH color indicator and a ß-lactamase inhibitor.

The expanded-spectrum ß-lactamase substrate, pH color indicator and an expanded-spectrum ß-lactamase inhibitor are as defined previously in the present patent application.

Typically, the reagent kit is used to detect the presence of expanded-spectrum ß-lactamase in a sample according to the method of the present invention.

Typically, when the specific ß-lactamase inhibitor is present in the reagent kit, the corresponding specific class of ß-lactamase, whether Ambler class A, B, C or D, may be determined.

Microtiter Plate:

According to another aspect of the invention, there is provided a microtiter plate comprising a well or a series of wells comprising expanded-spectrum ß-lactamase and cephalosporinase substrate selected from the group consisting of cephalosporins, aztreonam and cephamycins.

Typically, the microtiter plate may further comprise:
 a well or a series of wells which comprise a expanded-spectrum ß-lactamase substrate selected from the group consisting of cephalosporins, aztreonam and cephamycins and a ß-lactamase inhibitor of Ambler class A;
 a well or a series of wells which comprise a expanded-spectrum ß-lactamase substrate selected from the group consisting of cephalosporins, aztreonam and cephamycins and a ß-lactamase inhibitor of Ambler class B;
 a well or a series of wells which comprise an expanded-spectrum ß-lactamase substrate selected from the group consisting of cephalosporins aztreonam and cephamycins and a ß-lactamase inhibitor of Ambler class C; and
 a well or a series of wells which comprise a an expanded-spectrum ß-lactamase selected from the group consisting of cephalosporins, aztreonam and cephamycins and a ß-lactamase inhibitor of Ambler class D.

The microtiter plate may also contain a control well or a series of control wells which can be assayed and compared to the test samples.

Typically, the microtiter plate is a 96-well microtiter plate.

Devices other than microtiter plates may be used for this purpose. For example, a blotting paper in which the reagent kit (i.e. expanded-spectrum ß-lactamase substrate and the pH color indicator) has been incorporated may be used. Upon addition of the enzymatic suspension to the blotting paper, one can observe whether the paper changes color or not. Similarly, plastic galleries may be used. Indeed, the reagent kit may be included in these plastic galleries and then, upon addition of the enzymatic suspension into these galleries, one can observe whether there is a color change or not.

In order for the method of the invention to be performed, a pH color indicator, and a fraction of the enzymatic suspension to be tested are added to each well of the microtiter plate. Consequently, there is provided the use of a microtiter plate for detecting the presence of expanded-spectrum ß-lactamase-producing bacteria in a test sample according to the method of the present invention, whereby to each well is added at least a pH color indicator and a fraction of the enzymatic suspension to be tested. The microtiter plate is particularly well suited to determine the specific class of expanded-spectrum ß-lactamase present in a test sample.

Typically, if the pH color indicator is stable, the well or series of wells of the microtiter plate may also comprise the pH color indicator with the expanded-spectrum ß-lactamase substrate or with the expanded-spectrum ß-lactamase and the ß-lactamase inhibitor prior to performing the method of the invention. Alternatively, if the pH color indicator is not stable, it may be added to the well or series of wells afterwards.

The expanded-spectrum ß-lactamase substrate, the pH color indicator and the ß-lactamase inhibitor are as defined previously in the present patent application.

According to an embodiment, some of the components such as for example the expanded-spectrum ß-lactamase substrate and the ß-lactamase inhibitor (when present), may be directly bound to a solid surface of the microtiter plate. In this case, the remaining components (i.e. the pH color indicator) are added to the surface-bound expanded-spectrum ß-lactamase substrate and to the surface-bound ß-lactamase inhibitor (when present) in the microtiter plate with the test sample.

According to an embodiment, the microtiter plate as well as each of the elements used to perform the method of the invention may be enclosed within an individual container and all of the various containers may be placed within a single package along with instructions for observing whether expanded-spectrum ß-lactamase-producing bacteria can be found in the test sample.

The invention will further be illustrated in view of the following figures and examples.

FIGURES

ESBL producers (panel A) are as follows: *E. coli* FOR CTX-M-15 (1), *E. coli* GUE CTX-M-1 (2), *E. coli* DEV CTX-M-3 (3), *E. coli* GAL CTX-M-14 (4), *K. pneumoniae* ISS CTX-M-14 (5), *K. pneumoniae* DOU CTX-M-15 (6), *E. cloacea* MAZ CTX-M-15 (7), *E. coli* SHV-2a (8), *E. coli* SHV-12 (9), *E. coli* TEM-52 (10)

No ESBL producers are (panel B) as follows: *E. coli* BG 1106 6175 wild-type (1), *E. coli* BG 1106 6207 wild-type (2), *E. coli* BG 1106 6301 wild-type (3), *S. enterica* BG 1106 6187 wild-type (4), *K. oxytoca* BG 1106 6141 wild-type (5), *K. pneumoniae* BG 1106 7725 wild-type (6), *K. pneumoniae* BN 1113 0227 wild-type (7), *E. coli* MAC BG 1106 7257 penicillinase (8), *E. coli* BG 1106 5898 penicillinase (9), *E. coli* BN 1113 0228 penicillinase (10), *E. coli* BN 1113 0231 penicillinase (11), *E. cloacae* BG 1106 7746 wild-type (12), *C. freundii* BG 1106 7767 wild-type (13), *E. aerogenes* BN 1113 0225 wild-type (14), *M. morganii* BG 1106 5902 wild-type (15), *E. cloacae* BG 1106 7725 wild-type (16).

EXAMPLES

Example 1

Method (Acido-Colorimetric Test) According to the Invention

Six non-producers of ß-lactamases, seven producers of penicillinases without expanded-spectrum activity, five producers of cephalosporinases at low level, thirteen ESBL producers, two producers of expanded-spectrum class D enzymes (F) three producers of plasmid-encoded cephalosporinaes (G) six overproducers of chromosomal cephalosporinases, and (H) two producers of class B enzymes of the Applicant strain collection and of worldwide origin were included in the study (Table 1).

The strains were submitted to the method of the present invention as follows.

Equivalence of one ose of 10 µl of bacterial strains previously grown on trypticase soy agar was resuspended in Tris-HCL 20 mM+Triton X-100 2%+Tween 20 0.5% lysis buffer, vortexed for 1 min and further incubated at room temperature for 30 min. This bacterial suspension was centrifuged at 10,000 g at 4° C. for 5 min. and the supernatants were removed and placed on ice. 50 µl of this suspension supernatants (i.e. enzymatic suspension) were mixed in a well of a 96 well tray with 50 µl of a 1 ml solution made of 3 mg cefotaxime, phenol red solution pH 7.5 (i.e. the reagent kit).

The phenol red solution used by the Applicant was made by taking 2.2 ml of a concentrated phenol solution pH 8 (made from a mixture of phenol red 0.5% in distilled water) to which Applicant added 16.6 ml distilled water. The pH value was then adjusted to 7.5 by adding drops of 1 N NaOH solution.

Figure 1:
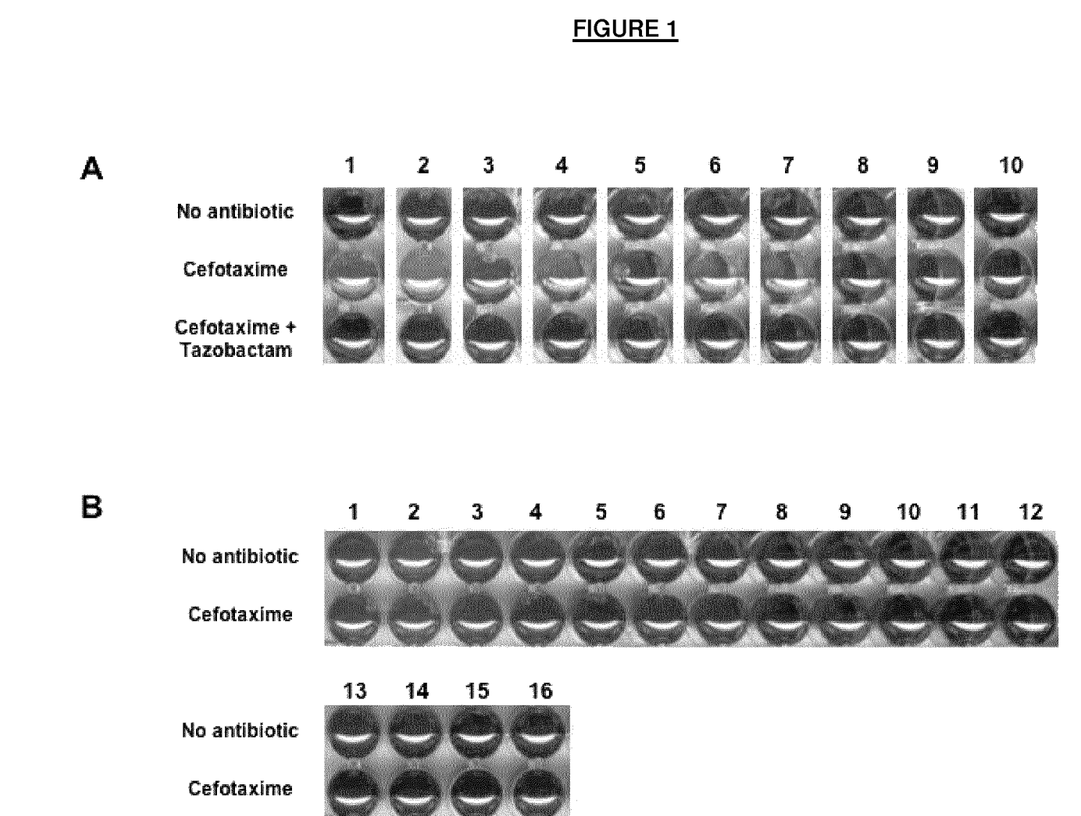
FIG. 1. Results for the method of detection of ESBL producers.

Mixtures of the reagent kit and tested enzymatic suspension were incubated at room temperature for 1.5 h. Suspensions of bacterial strains producing or not expanded-spectrum ß-lactamases (positive and negative controls) were also tested according to the method of the invention (Table 1). The color of the wells turn from red to yellow for all tested strains producing expanded-spectrum ß-lactamases whereas wells corresponding to bacterial extracts of isolates that did not produce expanded-spectrum ß-lactamases remained red. The color change from red to yellow was obtained as early as 15 min after the incubation start for CTX-M-15 producers. In most of the cases, a 40 min incubation time was sufficient for obtaining a frank color change for ESBL producers (FIG. 1). The color change although still positive was less frank with several isolates such as several SHV-type ESBL producers (FIG. 1). The testing was conducted as a blind study by a person who did not know which well comprised the ESBL producers. All tests were performed in triplicate with highly reproducible results.

Figure 2:
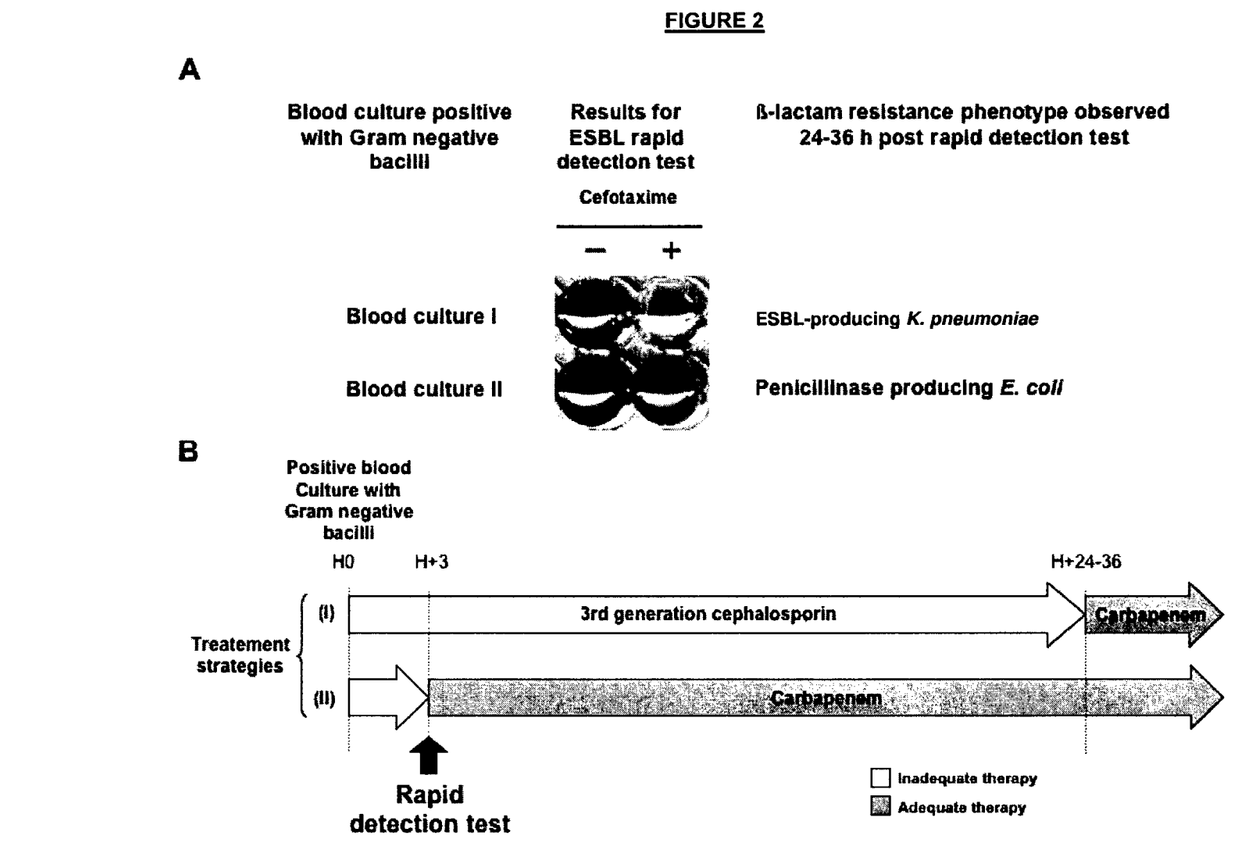
FIG. 2. Results (panel A) and strategy (panel B) for detection of ESBL producers directly from blood cultures. The test was applied to two positive blood cultures (panel A) and confirmatory identification of the ß-lactamase content was obtained 24-36 h later. The usage of the test permitted early detection of ESBL producer and adequate therapy (panel B).

Strategy and clinical usefulness of detection of ESBL producers directly from positive blood culture is shown in FIG. 2.

TABLE 1

Results of screening of (A) six non producers of β-lactamase, (B) seven producers of penicillinase (Ambler class A enzymes) wihout expanded-spectrum activity, (C) five producers of cephalosporinases at low level, (D) thirteen ESBL producers, (E) two producers of extanded-spectrum class D enzymes, (F) three producers of plasmid-encoded cephalosporinases, (G) six overproducers of chromosomal cephalosporinases, and (H) two producers of class B enzymes.

|   | Species | β-lactamase content | Origine | Detection test CTX | CTX + TAZ |
|---|---|---|---|---|---|
| A | *E. coli* BG 1106 6252 | Wild-type | Blood culture | − | − |
|   | *E. coli* BG 1106 6367 | Wild-type | Blood culture | − | − |
|   | *E. coli* BG 1106 6175 | Wild-type |   | − | − |
|   | *E. coli* BG 1106 6207 | Wild-type |   | − | − |
|   | *E. coli* BG 1106 6301 | Wild-type |   | − | − |

TABLE 1-continued

Results of screening of (A) six non producers of β-lactamase, (B) seven producers of penicillinase (Ambler class A enzymes) wihout expanded-spectrum activity, (C) five producers of cephalosporinases at low level, (D) thirteen ESBL producers, (E) two producers of extanded-spectrum class D enzymes, (F) three producers of plasmid-encoded cephalosporinases, (G) six overproducers of chromosomal cephalosporinases, and (H) two producers of class B enzymes.

|   | Species | β-lactamase content | Origine | Detection test CTX | CTX + TAZ |
|---|---|---|---|---|---|
|   | S. enterica BG 1106 6187 | Wild-type | Stool | − | − |
| B | K. oxytoca BG 1106 6141 | Wild-type | Urine | − | − |
|   | K. pneumoniae BG 1106 7725 | Wild-type | Mother milk | − | − |
|   | K. pneumoniae BG 1113 0227 | Wild-type | Urine | − | − |
|   | E. coli MAC BG 1106 7257 | Penicillinase | Sputum | − | − |
|   | E. coli BG 1106 5898 | Penicillinase | Blood culture | − | − |
|   | E. coli BG 1113 0228 | Penicillinase |  | − | − |
|   | E. coli BG 1113 0231 | Penicillinase | Urine | − | − |
| C | E. cloacae BG 1106 7746 | Wild-type | Sputum | − | − |
|   | C. freundii BG 1106 7767 | Wild-type | Urine | − | − |
|   | E. aerogenes BN 1113 0225 | Wild-type | Sputum | − | − |
|   | M. morganii BG 1106 5902 | Wild-type | Sputum | − | − |
|   | E. cloacae BG 1106 7725 | Wild-type | Mother milk | − | − |
| D | K. pneumoniae | CTX-M-15 | Blood culture | + | − |
|   | E. coli FOR | CTX-M-15 | Blood culture | + | − |
|   | E. coli GUE | CTX-M-1 | Blood culture | + | − |
|   | E. coli DEV | CTX-M-3 | Blood culture | + | − |
|   | E. coli GAL | CTX-M-14 | Blood culture | + | − |
|   | E. coli BRE | CTX-M-15 | Blood culture | + | − |
|   | K. pneumoniae ISS | CTX-M-14 | Blood culture | + | − |
| E | K. pneumoniae DOU | CTX-M-15 | Blood culture | + | − |
|   | E. cloacae MAZ | CTX-M-15 | Blood culture | + | − |
|   | E. coli LAN | SHV-2a |  | + | − |
|   | E. coli PAN | SHV-12 |  | + | − |
|   | K. pneumoniae PAS | TEM-3 |  | + | − |
|   | E. coli | TEM-52 |  | + | − |
|   | P. aeruginosa | OXA-14 |  | + | + |
|   | P. aeruriginosa | OXA-18 |  | + | + |
| F | E. coli Ec13 SYD | CMY-2 |  | + | + |
|   | K. pneumoniae FOR | DHA-2 |  | − | − |
|   | P. mirabilis | ACC-1 |  | − | − |
| G | E. cloacae AZA | overexpresion of chromosomal cephalosporinase |  | + | + |
|   | E. coli MAR | overexpression of chromosomal ephalosporinase | Bile | − | − |
|   | M. morgannii MAU | overexpression of chromosomal cephalosporinase | Urine | − | − |
|   | E. cloacae HUR | overexpression of chromosomal cephalosporinase | Blood culture | + | + |
|   | E. cloacae ARF | overexpression of chromosomal cephalosporinase |  | − | − |
|   | E. cloacae MEU | overexpression of chromosomal cephalosporinase | Blood culture | − | − |

TABLE 1-continued

Results of screening of (A) six non producers of β-lactamase, (B) seven producers of penicillinase (Ambler class A enzymes) wihout expanded-spectrum activity, (C) five producers of cephalosporinases at low level, (D) thirteen ESBL producers, (E) two producers of extanded-spectrum class D enzymes, (F) three producers of plasmid-encoded cephalosporinases, (G) six overproducers of chromosomal cephalosporinases, and (H) two producers of class B enzymes.

|   | Species | β-lactamase content | Origine | Detection test CTX | CTX + TAZ |
|---|---|---|---|---|---|
|   | C. freundii | overexpresion of chromosomic cephalosporinase + TEM-3 |  | + | − |
| H | E. colii | NDM-1 |  | + | + |
|   | K. pneumoniae | NDM-1 |  | + | + |

ND = Not determined
CTX = Cefotaxime (3 mg/ml),
TAZ = Tazobactam sulfate (4 mg/ml)

REFERENCES

Throughout this application, various references describe the state of the art to which this invention pertains. The disclosures of these references are hereby incorporated by reference into the present disclosure.

1. Zahar, J. R. et al. 2009. Addressing the challenge of extended-spectrum ß-lactamases. Curr Opin Investig Drugs, 10:172-180.
2. Poirel, L., T. Naas, and P. Nordmann. 2008. Genetic support of extended-spectrum ß-lactamases. Clin Microbiol Infect, 14 (suppl 1):75-81.
3. Poirel, L., T. Naas, and P. Nordmann. 2009. Diversity, epidemiology and genetics of class D ß-lactamases. Antimicrob Agents Chemother, 54:24-38.
4. Livermore D. M., and D. F. J. Brown. 2001. Detection of ß-lactamase-mediated resistance. J Antimicrob Chemother 48: suppl. S1, 59-64.
5. Shannon K., and I. Phillips. 1980. ß-Lactamase detection by three simple methods; intralactam, nitrocefin and acidimetric. J. Antimicrob. Chemother, 6:617-621.
6. Livermore D. M. 2008. Defining an extended-spectrum ß-lactamase. Clin Microbiol Infect, 14 (Suppl 1): 3-10.
7. Drieux, L. et al. 2008. Phenotypic detection of extended-spectrum ß-lactamase production in Enterobacteriaceae: a review and bench guide. Clin Microbiol Infect, 14 (suppl 1):90-13.
8. Pitout, D. D. and K. B Laupland. 2008. Extended-spectrum ß-lactamase-producing Enterobacteriaceae: an emerging public-health concern. Lancet Infect Dis, 8:159-166.
9. Giske et al. 2011. A sensitive and specific phenotypic assay for detection of metallo-ß-lactamases and KPC in Klebsiella pneumoniae with the suited of meropenem disks supplemented with aminophenylboronic acid, dipicolinic acid and cloxacillin. Clin Microbiol Infect, 17: 552-556.
10. Livermore, D. M. et al. 2011. Activities of NXL-104 combinations with ceftazidime and aztreonam against carbapenemase-producing Enterobacteriaceae. Antimicrob Agents Chemother, 55: 390-394.
11. Perez, F. et al. 2007. The continuing challenge of ESBLs. Curr Opin Pharmacol, 7:459-469.
12. Bradford, P. A. 2001. Extended-spectrum ß-lactamases in the 21$^{st}$ century: characterization, epidemiology, and detection of this important resistance threat. Clin Microbiol Rev, 14:933-951.
13. Yang, K. and B. J. Gugliemo. 2007. Diagnosis and treatment of extended-spectrum and AmpC ß-lactamase-producing organisms. Ann Pharmacother 41:1427-1435.
14. Harada, S., Y. Ishii, and K. Y. Yamaguchi. 2008. Extended-spectrum ß-lactamases: implications for the clinical laboratory and therapy. Korean J Lab Med, 28:401-412.
15. Clinical and Laboratory Standards Institute. 2010. Performance standards for antimicrobial susceptibility testing. CLSI M100-S20U. Update June 2010. Clinical and Laboratory Standards Institute, Wayne, Pa.

Example 2

Rapid Detection of Extended-Spectrum ß-Lactamase-Producing Enterobacteriaceae

Abstract

Enterobacterial strains producing clavulanic-acid inhibited extended-spectrum ß-lactamases (ESBLs) are increasingly reported worldwide. Conventional detection of ESBL production remains time-consuming (24 to 48 h). Therefore, the ESBL NDP (Nordmann/Dortet/Poirel) test was developed for a rapid identification of ESBLs in Enterobacteriaceae. This biochemical test was based on the in-vitro detection of a cephalosporin (cefotaxime) hydrolysis that is inhibited by tazobactam addition. The ESBL activity was evidenced by a color change (red-to-yellow) of a pH indicator (red phenol) due to carboxyl-acid formation resulting from cefotaxime hydrolysis that was reversed by addition of tazobactam (positive test). The NDP rapid ESBL test was applied to cultured strains (215 ESBL producers and 40 ESBL non-producers). Its sensitivity and specificity were 92.6% and 100%, respectively. It sensitivity (100%) was excellent for detection of CTX-M producers. A few ESBL producers (n=16) that remained susceptible to cefotaxime were not detected. The test was also evaluated on spiked blood cultures and showed excellent sensitivity and specificity (100% for both). The test was rapid (less than 1 h) and cost-effective. It can be implemented in any healthcare facility and is well adapted in particularly for infection control purposes.

Here, we propose a novel test, based on a technique designed to identify the hydrolysis of the ß-lactam ring of a cephalosporin (cefotaxime), which generates a carboxyl group, by acidifying a culture medium. It uses 96-well microtiter plates but is also adaptable to single tube. The acidity resulting from this hydrolysis is identified by the color change using a pH indicator (red phenol). Inhibition of ESBL activity is evidenced by adding tazobactam in a complementary well. We demonstrated that this test, applied either to bacterial colonies or directly to blood cultures, possessed good sensitivity and specificity.

Methods

Strain Collection

A total of 255 strains were used to evaluate the performance of the ESBL NDP (Nordmann/Dortet/Poirel) test. They were from various clinical origins (blood culture, urine, sputum, . . . ) and of worldwide origin (Tables 3A, B and C). Those strains had previously been characterized for their ß-lactamase content at the molecular level. This strain collection included producers of ESBLs (n=215) representing the most common ESBLs identified in clinical isolates (CTX-M, SHV, TEM, GES, and VEB enzymes) (Tables 3A and B). Negative controls (n=40) were made either of strains producing ß-lactamases possessing an extended spectrum activity, but whose activity is not inhibited by clavulanic acid/tazobactam (Table 3C). Negative controls also included strains expressing ß-lactamases possessing a narrow-spectrum of activity (Table 3C).

Susceptibility Testing

Susceptibility testing was performed by determining MIC values using the Etest® (AB bioMérieux; Solna, Sweden) on Mueller-Hinton agar plates at 37° C. and results were recorded according to US guidelines (CLSI), as updated in 2012 (2). The breakpoints for cefotaxime are susceptible (S)≤1 and resistant (R)≥4 µg/ml, and for ceftazidime S≤4 and R≥16 µg/ml.

ESBL NDP Test Using Cultured Strains

Strains were isolated on Mueller-Hinton agar (Biorad, Marnes-la-Coquette, France) and incubated at 37° C. for 16 h to 24 h before performing the NDP rapid ESBL test as follows. One calibrated inoculated loop (10 µl) of the tested strain was resuspended in 150 µl of 20 mM Tris-HCl lysis buffer previously distributed in Microbead tubes (Ultraclean Microbial DNA isolation kit Bead Tubes, MO BIO Laboratories, Carlsbad, USA). Mechanical lysis of bacteria was performed by strong agitation of Microbead tubes using a vortex adapter (MO BIO Laboratories) for 30 min at room temperature. This bacterial suspension was centrifuged at 10,000×g at room temperature for 5 min. Thirty µl of the supernatant was mixed in a well of a 96-well tray with 100 µl of a 1 ml solution made of 3 mg of purified cefotaxime sodium salt (Sigma-Aldrich, Saint-Quentin-Fallavier, France) in a pH 7.8 phenol red solution. Other cefotaxime concentrations, other ß-lactam molecules (ceftazidime, ceftriaxone, cefepime, aztreonam), and other pH indicators were tested, but giving less clear-cut results (data not shown). The phenol red solution was made by taking 2 ml of a concentrated pH 8 phenol solution (made from a mixture of phenol red 0.5% in distilled water) to which 16.6 ml of distilled water was added. The pH value was then adjusted to a 7.8 value by adding drops of a 1 N NaOH solution. Mixture of the phenol red solution and the enzymatic suspension being tested was incubated at 37° C. for 30 min. Similarly, culture extracts were analyzed in wells containing cefotaxime and tazobactam (4 mg/ml). Other concentrations of tazobactam and other ß-lactamase inhibitors were tested giving less clear results (data not shown). A test was considered as positive when the well containing cefotaxime alone turned from red to yellow/orange and the well containing cefotaxime supplemented with tazobactam remained red (unchanged color). This definition of test positivity will be applied throughout the study. Results were interpreted blindly by technicians who did not know which were the ESBL producers.

ESBL NDP Test Using Spiked Blood Cultures

Rapid detection of ESBL producers was attempted from spiked blood cultures which positivity was assessed using the BactAlert blood culture system (bioMérieux). A preliminary study showed that positivity of the blood cultures using this automated blood culture system corresponded to an inoculum ranging from $\sim5\times10^7$ to $\sim5\times10^9$ CFU/ml. This inoculum was reached after 24-48 h incubation in this BactAlert system. Strains were inoculated into blood culture system in presence of 10 ml of sterile blood. The panel of strains used for spiking blood cultures included either non-ESBL producers (n=24) or ESBL producers (n=64) (Table 4). Spiked blood cultures were made of $1\times10^3$ CFU of each strain and incubated 24 to 48 h before a positivity of the blood culture was detected by the BactAlert system. Then, 15 ml of spiked blood culture were transferred in a sterile tube and centrifuged at 1,500×g for 3 min to pellet the red blood cells. The supernatant was recovered and centrifuged for 15 min at 4,000×g to pellet the bacteria. The bacterial pellet was then resuspended in 500 µl of distilled water, transferred in 1.5 ml tube and thoroughly vortexed for 15 sec to lyse the remnant red blood cells and wash the bacterial pellet. After 5 min of centrifugation at 10,000×g, the bacterial pellet was resuspended in 150 µl of 20 mM Tris-HCl lysis buffer and distributed in beadtubes. The ESBL NDP test was then applied to this pellet as described above. Experiments were systematically performed in triplicate.

Results

ESBL NDP Test and Bacterial Cultures

Using the NDP Rapid ESBL test, when testing all CTX-M producers (n=147, Table 3 A), the color of the wells turned from red to yellow in presence of cefotaxime and remained red when tazobactam was added. The sensitivity of the test was excellent (100%). In all cases, MIC values of cefotaxime for those strains were high (>8 µg/ml). The test was less sensitive for detecting non-CTX-M ESBL producers since 17 out of the 68 tested strains (25%) among the ESBL producers failed to be detected (Table 3B). Negative results were observed in strains which had MIC values of cefotaxime lower than that the resistance breakpoint for that molecule (except for a few E. aerogenes isolates) (Table 3B). For all ESBL-producing isolates that hydrolyze cefotaxime (color change from red to yellow in the first well), the second well that contained tazobactam remained red (inhibition of hydrolysis), thus corresponding to a positive test. That result indicated the in-vitro inhibition of the ESBL activity by tazobactam. None of the wells containing bacterial extracts obtained from strains that did not produce ß-lactamases with extended-spectrum activity had a positive test (Table 3). A few ESBL-negative strains producing ß-lactamases hydrolyzing cefotaxime (overproduced cephalosporinases) (Table 3B) gave a red-to-yellow color change in wells containing cefotaxime. However, this color change was also observed in wells containing cefotaxime supplemented with tazobactam, indicating that the hydrolytic activity of those enzymes was not inhibited by tazobactam, thus corresponding to a negative test) (Table 3C). The overall sensitivity and specificity of the ESBL NDP test were 92.6% and 100% respectively. The ESBL NDP test was able to differentiate between ESBL producers and strains being resistant to extended-spectrum cephalosporins by other mechanisms, or from those being susceptible to expanded-spectrum cephalosporins and therefore not producing an ESBL (Table 3C). Noteworthy, those isolates combining ESBL production together with overproduced (chromosomal or plasmid-mediated) AmpC gave positive results.

The red-to-yellow color change was obtained quickly (1 to 5 min after the start of incubation) for most CTX-M producers. Overall, a 15-min incubation time was sufficient to obtain a frank color change for all CTX-M producers (n=147). However, interpretable results were always obtained for all ESBL producers in less than 30 min.

ESBL NDP Test and Blood Cultures

The ESBL NDP test was used directly from blood cultures inoculated with ESBL (n=64) and non-ESBL producers (n=24) (Table 4). The sensitivity and specificity of the test were 100% in that case. The total amount of time required to obtain results using spiked blood cultures was less than two hours.

Discussion

The ESBL NDP test combines multiple advantages. It is cheap, rapid, sensitive, and specific. It is particularly effective for detecting CTX-M producers that currently account for most of the ESBLs identified worldwide. The reasons of the lack of detection of several ESBL producers in particularly of the TEM and SHV series remain to be elucidated. This may result from a weak hydrolysis of cefotaxime, but also from a low-level production of the ESBL which is related to low MIC values of cefotaxime. All strains overproducing an AmpC but ESBL negative gave negative results. This resulted from two possibilities; (i) no (or very poor) hydrolysis of cefotaxime by the AmpC leading to two red wells, or (ii) hydrolysis of cefotaxime not inhibited by clavulacid acid or tazobactam in accordance with the AmpC property, leading to two yellow/orange wells. Noteworthy, several isolates positive for ESBL production and overexpressing their chromosome-encoded cephalosporinase have been tested. All those strains were positive for the hydrolysis of cefotaxime due to the action of the ESBL but this hydrolysis was well inhibited by tazobactam, thus giving a positive result. However, we cannot rule out that some ESBL-positive and AmpC-overproducing isolates could give a positive result for cefotaxime plus tazobactam, if the corresponding AmpC hydrolyses cefotaxime at high level (leading to a false-negative result).

Interestingly, we showed that this assay can be easily implemented for detection of ESBL-producing isolates from blood cultures. Of note, the overall sensitivity of the Rapid ESBL NDP test was even higher (reaching 100%) when using this blood culture protocol. These results could be explained by the increased inoculum recovered from blood culture experiments as compared to those recovered during pure culture experiments.

This test can be used to search for ESBL producers among (i) bacteria grown in blood cultures and/or (ii) bacterial colonies grown on selective or non-selective media prior to any antibiotic susceptibility testing. This test may therefore find an excellent application in countries where a high incidence of ESBL producers (mostly CTX-M) occurs, such as in many Asian countries. Use of this test might significantly improve the outcome of patients infected with ESBL producers, by supporting a better antimicrobial stewardship through the rapid and accurate identification of ESBL-producing isolates. Interestingly a positive cefotaxime hydrolysis (color change from red to yellow in cefotaxime-containing well) was always associated with expression of either an ESBL or a plasmid-mediated cephalosporinase and high MIC values for cefotaxime and above the resistance breakpoints (Tables 3A, B, C; Table 4). Although a negative result could not exclude the presence of a broad-spectrum cephalosporin-resistant strain resulting from porin deficiency associated with a low-level ß-lactamase activity, a positive result with ESBL NDP test may have an important clinical signification for excluding the choice of expanded-spectrum cephalsporins for treating infected patients, and retaining a carbapenem-containing regimen.

It is admitted that ESBL detection is particularly useful for hygiene and infection control. A rapid identification of carriage of ESBL producers, in particularly when a cephalosporin-resistant isolate has been obtained using chromogenic screening media, may help to implement adequate hygiene measures rapidly that will further prevent the development of nosocomial outbreaks. Using the ESBL NDP test directly from colonies grown from those screening media would provide a significant gain of time (at least 24 h) as compared to phenotypic-based techniques. This may have an important value for prevention of outbreaks, particularly in high risk units (i.e. intensive care units . . . ) and for cost savings, in particular those costs resulting from dedicated staff. In addition, the ESBL NDP test used as a screening test is much cheaper than molecular-based techniques. This feature is of outmost importance for many developing countries.

The ESBL NDP test would also support novel antibiotic development by facilitating patient enrollment in pivotal clinical trials. Results from the ESBL NDP test can select the strains to be further tested by PCR and/or submitted to sequencing for a detailed identification of the genes at the molecular level.

TABLE 3A

Detection of CTX-M producing isolates using the NDP Rapid ESBL test

| Phenotype of β-lactam resistance | β-Lactamase content | Species | n | Test CTX | Test CTX + TZB | MICs range (µg/ml) CTX | CTX + CLA | CAZ | CAZ + CLA |
|---|---|---|---|---|---|---|---|---|---|
| Extended srectrum β-lactamases | CTX-M group 1 | | | | | | | | |
| | CTX-M-1 | E. coli | 16 | + | − | >16 | 0.04-0.12 | 0.5-2 | 0.06-0.19 |
| | | S. enterica | 1 | + | − | >16 | 0.06 | 0.75 | 0.12 |
| | CTX-M-3 | E. coli | 1 | + | − | >16 | >1 | 4 | 1 |
| | | K. pneumoniae | 1 | + | − | >16 | 0.5 | 1.5 | 0.19 |
| | CTX-M-15 | E. coli | 46 | + | − | 8->16 | 0.06-1 | 0.5-24 | 0.12-0.19 |
| | | K. pneumoniae | 28 | + | − | >16 | 0.03-0.12 | 2->32 | 0.12-0.19 |
| | | E. cloacae | 17 | + | − | >16 | 0.12-0.25 | 2-16 | 0.25-0.5 |
| | | C. freundii | 3 | + | − | >16 | 0.12-0.25 | 8->32 | 0.25-0.75 |
| | | P. mirabilis | 1 | + | − | >16 | 0.09 | 8 | 0.19 |
| | CTX-M-28 | E. coli | 1 | + | − | >16 | 0.06 | 8 | 0.09 |
| | CTX-M-32 | E. coli | 1 | + | − | >16 | 0.09 | 6 | 0.12 |

TABLE 3A-continued

Detection of CTX-M producing isolates using the NDP Rapid ESBL test

| Phenotype of β-lactam resistance | β-Lactamase content | Species | n | Test CTX | Test CTX + TZB | MICs range (μg/ml) CTX | CTX + CLA | CAZ | CAZ + CLA |
|---|---|---|---|---|---|---|---|---|---|
| CTX-M group 2 | CTX-M-2 | E. coli | 3 | + | − | >16 | 0.05-0.06 | 1.5-4 | 0.06-0.25 |
| | CTX-M-97 | E. coli | 1 | + | − | >16 | 0.04 | 2 | 0.09 |
| CTX-M group 9 | CTX-M-14 | E. coli | 15 | + | − | >16 | 0.03-0.12 | 0.5-4 | 0.09-0.25 |
| | | K. pneumoniae | 3 | + | − | >16 | 0.04-0.12 | 0.5-6 | 0.12-0.25 |
| | | E. cloacae | 1 | + | − | >16 | >1 | 8 | >1 |
| | | P. mirabilis | 1 | + | − | >16 | 0.09 | 0.75 | 0.12 |
| | CTX-M-27 | E. coli | 6 | + | − | >16 | 0.03-0.09 | 0.5-4 | 0.09-0.25 |
| | CTX-M-9 | E. coli | 1 | + | − | >16 | 0.06 | 0.19 | 0.09 |

CTX, cefotaxime; TZB, tazobactam; CAZ, ceftazidime; CLA, clavulanic acid
(+) and (−) referred to color change being, red to yellow or unchanged, respectively

TABLE 3B

Detection of TEM-type, SHV-type, GES-type, VEB-type and PER-type producing isolates using the NDP Rapid ESBL test.

| Phenotype of β-lactam resistance | β-Lactamase content | | Species | n | Test CTX | Test CTX + TZB | MICs range (μg/ml) CTX | CTX + CLA | CAZ | CAZ + CLA |
|---|---|---|---|---|---|---|---|---|---|---|
| Extended srectrum β-lactamases | TEM-type | TEM-3 | K. pneumoniae | 3 | + | − | 4->16 | 0.06-0.09 | 4->32 | 0.06-0.09 |
| | | | E. cloacae | 2 | + | − | >16 | 0.12-0.38 | >16 | 0.12-0.5 |
| | | | C. freundii | 1 | + | − | >16 | 0.12 | >16 | 0.25 |
| | | TEM-12 | E. coli | 1 | − | − | 0.5 | 0.06 | 8 | 0.09 |
| | | TEM-21 | P. mirabilis | 1 | + | − | 0.25 | 0.06 | 4 | 0.12 |
| | | TEM-24 | E. aerogenes | 6 | − | − | 0.5-8 | 0.5-8 | 8->32 | 0.09-8 |
| | | | P. stuartii | 1 | − | − | 0.5 | 0.25 | 8 | 0.09 |
| | | TEM-29 | E. coli | 2 | − | − | 0.25 | 0.06 | 4 | 0.12 |
| | | TEM-52 | E. coli | 8 | + | − | 8->16 | 0.03-0.09 | 8->32 | 0.09 |
| | | | K. pneumoniae | 2 | + | − | >16 | 0.04-0.12 | >32 | 0.12-0.19 |
| | | | P. mirabilis | 1 | + | − | >16 | 0.09 | 16 | 0.12 |
| | | TEM-121 | E. aerogenes | 1 | − | − | <0.06 | <0.06 | >32 | 32 |
| | | TEM-133 | E. coli | 1 | − | − | 0.19 | 0.06 | 12 | 0.09 |
| | SHV-type | SHV-2a | K. pneumoniae | 4 | + | − | 8->16 | 0.06-0.09 | 2-4 | 0.06-0.19 |
| | | | K. pneumoniae | 2 | − | − | 1 | 0.03-0.06 | 1-4 | 0.03-0.12 |
| | | | E. coli | 3 | + | − | 8->16 | 0.06-0.09 | 2-4 | 0.06-0.19 |
| | | SHV-3 | E. coli | 1 | + | − | 12 | 0.02 | >32 | 0.09 |
| | | SHV-5 | K. pneumoniae | 2 | + | − | >16 | 0.03-0.12 | 16-32 | 0.09-0.25 |
| | | | E. cloacae | 1 | + | − | >16 | 0.38 | >32 | 0.5 |
| | | SHV-12 | E. coli | 6 | + | − | >16 | 0.05-0.06 | 8->32 | 0.06-0.25 |
| | | | E. coli | 1 | − | − | 0.75 | 0.06 | 8 | 0.12 |
| | | | K. pneumoniae | 2 | + | − | 2-8 | 0.03-0.06 | 16-32 | 0.12-0.19 |
| | | | K. pneumoniae | 1 | − | − | 1 | 0.04 | 8 | 0.12 |
| | | | E. cloacae | 6 | + | − | 8->16 | 0.38->1 | 16->32 | 0.5->4 |
| | | SHV-28 | K. pneumoniae | 3 | + | − | >16 | 0.12-0.25 | >32 | 0.09-0.25 |
| | GES | GES-1 | K. pneumoniae | 1 | + | − | 0.5 | 0.06 | 4 | 0.5 |
| | | GES-5 | E. cloacae | 1 | + | − | >16 | >1 | >32 | >1 |
| | VEB | VEB-1 | E. coli | 1 | + | − | 8 | 0.12 | >32 | 0.25 |
| | | | E. cloacae | 1 | + | − | 16 | 0.5 | >32 | 0.5 |
| | PER | PER-1 | P. mirabilis | 1 | + | − | >16 | 0.12 | >32 | 0.25 |
| | | PER-1 | E. cloacae | 1 | + | − | >16 | >1 | >32 | >1 |

CTX, cefotaxime; TZB, tazobactam; CAZ, ceftazidime; CLA, clavulanic acid
(+) and (−) referred to color change being, red to yellow or unchanged, respectively

TABLE 3C

Detection of non-ESBL producing isolates using the NDP Rapid ESBL test

| Phenotype of β-lactam resistance | β-Lactamase content | Species | n | Test CTX | Test CTX + TZB | MICs range (µg/ml) CTX | CTX + CLA | CAZ | CAZ + CLA |
|---|---|---|---|---|---|---|---|---|---|
| No resistance | Wild-type | E. coli | 5 | − | − | 0.02-0.04 | ND | 0.05-0.19 | ND |
|  | Wild-type | S. enterica | 1 | − | − | 0.05 | ND | 0.19 | ND |
| Penicillinase | TEM-1 | E. coli | 5 | − | − | 0.03-0.09 | ND | 0.09-0.12 | ND |
|  | Wild-type | K. pneumoniae | 2 | − | − | 0.02-0.03 | ND | 0.03 | ND |
|  | Wild-type | K. oxytoca | 1 | − | − | 0.03 | ND | 0.06 | ND |
| Chromosome-encoded cephalosporinase | Wild-type | E. cloacae | 5 | − | − | 0.09-0.5 | ND | 0.12-0.38 | ND |
|  | Wild-type | E. aerogenes | 1 | − | − | 0.094 | ND | 0.25 | ND |
|  | Wild-type | M. morganii | 2 | − | − | 0.03-0.75 | ND | 0.09-1 | ND |
|  | Wild-type | C. freundii | 1 | − | − | 0.12 | ND | 0.25 | ND |
|  | Wild-type | C. brakii | 1 | − | − | 0.12 | ND | 0.25 | ND |
|  | Wild-type | S. marcescens | 2 | − | − | 0.19-0.75 | ND | 0.09 | ND |
|  | Wild-type | S. ficaria | 1 | − | − | 0.12 | ND | 0.09 | ND |
| Acquired cephalosporinase | DHA-1 | E. coli | 1 | − | − | 0.25 | 1 | 1 | 2 |
|  | DHA-1 | K. pneumoniae | 1 | − | − | >16 | >1 | >32 | >4 |
|  | DHA-2 | K. pneumoniae | 1 | + | + | >16 | >1 | >32 | >4 |
|  | ACC-1 | E. coli | 1 | − | − | >16 | >1 | >32 | >4 |
|  | ACC-1 | E. coli | 1 | + | + | >16 | >1 | >32 | >4 |
|  | ACC-1 | P. mirabilis | 1 | − | − | >16 | >1 | >32 | >4 |
|  | CMY-2 | E. coli | 1 | + | + | >16 | >1 | >32 | >4 |
| Overexpressed chromosome-encoded cephalosporinase |  | E. cloacae | 3 | + | + | >16 | >1 | >32 | >4 |
|  |  | E. cloacae | 2 | − | − | >16 | >1 | >32 | >4 |
|  |  | E. sakazakii | 1 | − | − | >16 | >1 | >32 | >4 |

ND, not determined
CTX, cefotaxime; TZB, tazobactam; CAZ, ceftazidime; CLA, clavulanic acid
(+) and (−) referred to color change being, red to yellow or unchanged, respectively

TABLE 4

Detection of non-ESBL and ESBL producers in spiked blood cultures using the NDP rapid ESBL test

|  | β-lactamase | Species | Bacterial concentration in blood culture | ESBL NDP Test from: Blood culture CTX | CTX + TZB | Colonies CTX | CTX + TZB |
|---|---|---|---|---|---|---|---|
| Control strains | Wild-type | E. coli BG 1106 6252 | $8.0 \times 10^8$ | − | − | − | − |
|  |  | E. coli BG 1106 6367 | $7.0 \times 10^8$ | − | − | − | − |
|  |  | E. coli BG 1107 8873 | $5.2 \times 10^9$ | − | − | − | − |
|  | Penicillinase | E. coli BG 1106 5698 | $2.0 \times 10^9$ | − | − | − | − |
|  |  | E. coli BG 1106 7202 | $1.3 \times 10^9$ | − | − | − | − |
|  |  | E. coli BG 1108 6157 | $1.2 \times 10^9$ | − | − | − | − |
|  |  | K. pneumoniae BG 1202 5484 | $4.0 \times 10^8$ | − | − | − | − |
|  | Wild-type | E. cloacae BG 1106 7746 | $1.4 \times 10^9$ | − | − | − | − |
|  |  | E. cloacae BG 1106 7725 | $5.2 \times 10^8$ | − | − | − | − |
|  |  | E. cloacae BG 1107 4118 | $5.0 \times 10^8$ | − | − | − | − |
|  |  | E. aerogenes BN 1113 0225 | $1.0 \times 10^9$ | − | − | − | − |
|  |  | M. morganii BG 1106 5902 | $1.7 \times 10^9$ | − | − | − | − |
|  |  | M. morganii BG 1117 0617 | $1.4 \times 10^9$ | − | − | − | − |
|  |  | C. freundii BG 1106 7767 | $8.8 \times 10^8$ | − | − | − | − |
|  |  | S. marcescens BG 1107 4243 | $8.0 \times 10^8$ | − | − | − | − |
|  |  | S. marcescens BN 1201 0816 | $3.8 \times 10^9$ | − | − | − | − |
|  |  | S. ficaria CIP 104255 | $2.1 \times 10^9$ | − | − | − | − |
| Acquired cephalosporinase | DHA-1 | E. coli GOU | $9.7 \times 10^9$ | − | − | − | − |
|  | DHA-1 | K. pneumoniae ANG | $1.1 \times 10^8$ | − | − | − | − |
|  | DHA-2 | K. pneumoniae FOR | $2.1 \times 10^9$ | + | + | + | + |
|  | ACC-1 | E. coli (Belgium) | $7.8 \times 10^7$ | − | − | − | − |
|  | ACC-1 | E. coli LOU | $2.3 \times 10^9$ | + | + | + | + |
|  | ACC-1 | P. mirabilis BIK | $8.0 \times 10^7$ | − | − | − | − |
|  | CMY-2 | E. coli Ec13 SYD | $1.8 \times 10^9$ | + | + | + | + |
| TEM producing strains | TEM-3 | K. pneumoniae 09.200 | $1.5 \times 10^8$ | + | − | + | − |
|  |  | K. pneumoniae 09.138 | $3.0 \times 10^8$ | + | − | + | − |
|  | TEM-21 | P. mirabilis 09.177 | $1.2 \times 10^9$ | + | − | + | − |
|  | TEM-52 | E. coli 09.11 | $2.7 \times 10^9$ | + | − | + | − |
|  |  | E. coli 09.40 | $1.3 \times 10^9$ | + | − | + | − |
|  |  | E. coli 09.66 | $1.8 \times 10^9$ | + | − | + | − |
|  |  | E. coli 09.73 | $1.1 \times 10^9$ | + | − | + | − |

TABLE 4-continued

Detection of non-ESBL and ESBL producers in spiked blood cultures using the NDP rapid ESBL test

|  |  |  | Bacterial concentration in blood culture | ESBL NDP Test from: | | | |
|---|---|---|---|---|---|---|---|
|  |  |  |  | Blood culture | | Colonies | |
|  | β-lactamase | Species |  | CTX | CTX + TZB | CTX | CTX + TZB |
|  |  | E. coli 09.92 | $6.0 \times 10^8$ | + | − | + | − |
|  |  | E. coli 09.124 | $1.0 \times 10^9$ | + | − | + | − |
|  |  | E. coli 09.225 | $2.0 \times 10^8$ | + | − | + | − |
|  |  | K. pneumoniae 09.162 | $8.0 \times 10^8$ | + | − | + | − |
|  |  | K. pneumoniae 09.169 | $1.0 \times 10^9$ | + | − | + | − |
|  |  | P. mirabilis 09.128 | $5.0 \times 10^8$ | + | − | + | − |
|  | TEM-121 | E. aerogenes E2O15 | $3.0 \times 10^8$ | + | − | − | − |
|  | TEM-133 | E. coli 09.123 | $1.7 \times 10^9$ | + | − | − | − |
| SHV-producing strains | SHV-2a | E. coli 09.187 | $1.3 \times 10^9$ | + | − | + | − |
|  |  | E. coli 09.207 | $4.0 \times 10^8$ | + | − | + | − |
|  |  | K. pneumoniae 09.99 | $1.7 \times 10^9$ | + | − | + | − |
|  |  | K. pneumoniae 09.127 | $9.0 \times 10^8$ | + | − | + | − |
|  |  | K. pneumoniae 09.181 | $1.3 \times 10^9$ | + | − | + | − |
|  |  | K. pneumoniae 09.190 | $1.4 \times 10^9$ | + | − | − | − |
|  | SHV-3 | E. coli A7R5 | $1.4 \times 10^8$ | + | − | + | − |
|  | SHV-5 | K. pneumoniae 09.60 | $1.6 \times 10^9$ | + | − | + | − |
|  |  | K. pneumoniae 09.217 | $9.0 \times 10^8$ | + | − | + | − |
|  | SHV-12 | E. coli 09.41 | $1.3 \times 10^9$ | + | − | + | − |
|  |  | E. coli 09.79 | $1.4 \times 10^9$ | + | − | + | − |
|  |  | E. coli 09.129 | $1.7 \times 10^9$ | + | − | + | − |
|  |  | E. coli 09.173 | $3.2 \times 10^9$ | + | − | + | − |
|  |  | E. coli 09.193 | $2.6 \times 10^9$ | + | − | + | − |
|  |  | K. pneumoniae 09.45 | $2.6 \times 10^9$ | + | − | + | − |
|  |  | K. pneumoniae 09.158 | $1.9 \times 10^9$ | + | − | + | − |
|  |  | E. cloacae 09.57 | $1.0 \times 10^9$ | + | − | + | − |
| CTX-M-producing strains | CTX-M-1 | E. coli 10.36 | $1.8 \times 10^9$ | + | − | + | − |
|  |  | E. coli 10.38 | $1.7 \times 10^9$ | + | − | + | − |
|  |  | S. thyphimurium 10.81 | $2.0 \times 10^9$ | + | − | + | − |
|  |  | E. coli 10.95 | $1.0 \times 10^9$ | + | − | + | − |
|  |  | E. coli 10.104 | $3.3 \times 10^9$ | + | − | + | − |
|  | CTX-M-14 | E. coli 10.46 | $7.8 \times 10^8$ | + | − | + | − |
|  |  | E. coli 10.124 | $5.2 \times 10^8$ | + | − | + | − |
|  |  | E. coli 10.11 | $1.9 \times 10^9$ | + | − | + | − |
|  |  | E. coli 10.13 | $1.6 \times 10^9$ | + | − | + | − |
|  |  | E. coli 10.32 | $2.7 \times 10^9$ | + | − | + | − |
|  | CTX-M-15 | E. coli 10.16 | $2.0 \times 10^9$ | + | − | + | − |
|  |  | E. coli 10.33 | $3.7 \times 10^9$ | + | − | + | − |
|  |  | E. coli 10.43 | $3.6 \times 10^9$ | + | − | + | − |
|  |  | E. coli 10.49 | $1.0 \times 10^7$ | + | − | + | − |
|  |  | E. coli 10.74 | $9.6 \times 10^8$ | + | − | + | − |
|  |  | E. cloacae 10.75 | $3.8 \times 10^8$ | + | − | + | − |
|  |  | E. cloacae 10.87 | $2.2 \times 10^9$ | + | − | + | − |
|  |  | K. pneumoniae SHI | $1.5 \times 10^9$ | + | − | + | − |
|  |  | K. pneumoniae MEK | $3.4 \times 10^8$ | + | − | + | − |
|  | CTX-M-2 | E. coli 10.121 | $1.9 \times 10^9$ | + | − | + | − |
|  |  | E. coli 10.23 | $1.2 \times 10^9$ | + | − | + | − |
|  |  | E. coli 10.132 | $1.4 \times 10^9$ | + | − | + | − |
|  | CTX-M-27 | E. coli 10.73 | $5.0 \times 10^8$ | + | − | + | − |
|  |  | E. coli 10.178 | $1.3 \times 10^9$ | + | − | + | − |
|  |  | E. coli 10.198 | $2.7 \times 10^9$ | + | − | + | − |
|  |  | E. coli 10.204 | $1.7 \times 10^9$ | + | − | + | − |
|  |  | E. coli 10.207 | $2.3 \times 10^9$ | + | − | + | − |
|  | CTX-M-3 | E. coli 10.130 | $1.9 \times 10^9$ | + | − | + | − |
|  |  | K. pneumoniae 10.159 | $2.1 \times 10^9$ | + | − | + | − |
|  | CTX-M-32 | E. coli 10.64 | $1.0 \times 10^9$ | + | − | + | − |
|  | CTX-M-28 | E. coli C5O52 | $1.0 \times 10^9$ | + | − | + | − |
|  | CTX-M-9 | E. coli 10.53 | $2.2 \times 10^9$ | + | − | + | − |

CTX, cefotaxime; TZB, tazobactam; CAZ, ceftazidime; CLA, clavulanic acid
(+) and (−) referred to color change being, red to yellow or unchanged, respectively

The invention claimed is:

1. A method for detecting the presence of expanded-spectrum ß-lactamase-producing bacteria in a blood or urine sample, said method comprising the steps of:

a) performing cell lysis on the blood or urine sample in order to obtain an enzymatic suspension, wherein said bacteria in said blood or urine sample are not cultured to isolate said bacteria prior to step a);

b) reacting a fraction of the enzymatic suspension obtained in step a) with a reagent kit, said reagent kit comprising
an expanded-spectrum ß-lactamase (EBSL) substrate selected from cephalosporins and aztreonam; and,
a pH color indicator which will change color when the pH of the reaction mixture is from 6.4 and 8.4,
wherein a color change visually observed within 5 minutes to 120 minutes after the beginning of step b)

indicates the presence of expanded-spectrum ß-lactamase-producing bacteria in the blood or urine sample.

2. The method according to claim 1, wherein the expanded-spectrum ß-lactamase-producing bacteria are selected from the group consisting of *Acinetobacter, Aeromonas, Bacillus, Bacteroides, Citrobacter, Enterobacter, Escherichia, Klebsiella, Morganella, Pandoreae, Proteus, Providencia, Pseudomonas, Ralstonia, Raoultella, Salmonella, Serratia, Shewanella, Shigella* and *Stenotrophomonas*.

3. The method according to claim 1, wherein reaction in step b) is carried out at a temperature between 15° C. and 40° C.

4. A method according to claim 1,
wherein the ESBL substrate is cefotaxime,
wherein the pH color indicator is phenol red, and
wherein the color change is from red to yellow.

5. The method according to claim 1, wherein reaction in step b) is carried out at a temperature between 20° C. and 37° C.

6. The method according to claim 1, wherein the reaction in step b) is carried out over a period of time sufficient to observe a color change.

7. The method according to claim 1, wherein the reaction in step b) is carried out over a period of time between 20 minutes and 40 minutes.

8. The method according to claim 1, wherein the expanded-spectrum ß-lactamase substrate which is a cephalosporin or an aztreonam is selected from the group consisting of cefotaxime, ceftriaxone, ceftazidime, cefepime, and cefpirome.

* * * * *